(12) United States Patent
Kikuchi

(10) Patent No.: US 6,950,186 B2
(45) Date of Patent: Sep. 27, 2005

(54) POLARIZATION ANALYZING METHOD

(75) Inventor: Toshihiko Kikuchi, Nirasaki (JP)

(73) Assignee: Tokyo Electron Limited, Tokyo (JP)

( * ) Notice: Subject to any disclaimer, the term of this patent is extended or adjusted under 35 U.S.C. 154(b) by 0 days.

(21) Appl. No.: 10/909,458

(22) Filed: Aug. 3, 2004

(65) Prior Publication Data
US 2005/0007592 A1 Jan. 13, 2005

Related U.S. Application Data

(63) Continuation of application No. PCT/JP03/01370, filed on Feb. 10, 2003.

(30) Foreign Application Priority Data

Feb. 18, 2002 (JP) ........................ 2002-040506

(51) Int. Cl.[7] .................................. G01J 4/00
(52) U.S. Cl. ...................... 356/369; 356/630
(58) Field of Search ................ 356/369, 364, 356/630

(56) References Cited

U.S. PATENT DOCUMENTS 6,233,046 B1 * 5/2001 Alba et al. ............... 356/38
6,590,656 B2 * 7/2003 Xu et al. ............... 356/369

FOREIGN PATENT DOCUMENTS

JP 11-316187 11/1999

* cited by examiner

Primary Examiner—Gregory J. Toatley, Jr.
Assistant Examiner—Roy M. Punnoose
(74) Attorney, Agent, or Firm—Oblon, Spivak, McClelland, Maier & Neustadt, P.C.

(57) ABSTRACT

Assuming that the s-polarized light of the incident light is reflected from the interface of the layer B, and the p-polarized light is reflected from the interface of the layer D, each amplitude reflectivity of Rs and Rp are calculated, and tan ψ of a function of the amplitude ratio ψ of the p-polarization component to the s-polarization component and cos Δ of a function of the phase difference Δ between the p-polarization component and the s-polarization component are calculated, thereby creating reference data. The thickness tA of the oxide film 301 is determined on the basis of the reference data. Thus, the thickness and cross section shape of the film formed on the multilayer interconnection are measured in a nondestructive manner with high throughput.

11 Claims, 6 Drawing Sheets (a) P-POLARIZED LIGHT (a) S-POLARIZED LIGHT (a) P-POLARIZED LIGHT

POLARIZATION ANALYZING METHOD

This application is a Continuation Application of PCT International Application No. PCT/JP03/01370 filed on Feb. 10, 2003, which designated the United States.

FIELD OF THE INVENTION

The present invention relates to a polarization analyzing method; and, more particularly, to a polarization analyzing method suitable for measuring a film thickness or a cross sectional shape such as an etching shape in a semiconductor device manufacturing process.

BACKGROUND OF THE INVENTION

Conventionally, an optical film thickness measurement using an ellipsometer has been employed, for example, in inspecting a film thickness in a semiconductor device manufacturing process.

FIG. 2 schematically illustrates such an optical film thickness measurement using the ellipsometer. As shown in the drawing, in the optical film thickness measurement using the ellipsometer, light emanating from a light source 101 passes through respective optical elements, i.e., a polarizer 102 for regulating a polarization state and a compensation plate 103 for regulating a phase, whereby elliptically polarized incident light is formed and illuminated on a sample 107.

Then, by installing an analyzer 104 for examining the polarization state, a spectroscope 105 for selecting light of a predetermined wavelength, and a detector 106 along an optical path of the light reflected from the sample 107, the polarization state is measured for each wavelength of the reflected light and a spectrum is obtained.

For example, as shown in FIG. 3 in case of measuring a thickness of an oxide film 201 (e.g., a gate oxide film) formed on a Si substrate 202, an elliptically polarized incident light illuminated as described above at an angle θ0 from the air 200 (refractive index=N0) is reflected from a surface of the oxide film 201 (refractive index=N1) and, at the same time, most of the incident light is transmitted into the oxide film 201. Further, the light transmitted into the oxide film 201 is reflected off an interface (a substrate surface) of the Si substrate 202 (refractive index=N2) and returns to the air 200 from the inside of the oxide film 201 to thereby interfere with the light reflected from the surface of the oxide film 201 such that the polarization of the light returned to the air by being reflected from the interface of the Si substrate 202 interferes with that of the light reflected from the surface of the oxide film 201.

As to the aforementioned light, after calculating p-polarization component and s-polarization component, a film thickness is calculated from a phase difference $\Delta$ and an amplitude ratio $\psi$ thereof.

P-polarization component $r_{1p}$ and s-polarization component $r_{1s}$ of the light reflected from the surface of the Si substrate 202 are respectively calculated by the following equations.

$$r_{1p}=(n_2\cos\theta_1-n_1\cos\theta_2)/(n_2\cos\theta_1+n_1\cos\theta_2)$$

$$r_{1s}=(n_1\cos\theta_1-n_2\cos\theta_2)/(n_1\cos\theta_1+n_2\cos\theta_2)$$

Further, polarization states of p-polarization component $R_p$ and s-polarization component $R_s$ of detected light are obtained by the following equations based on the polarization components $r_{1p}$ and $r_{1s}$ described above and p-polarization component $r_{0p}$ and s-polarization component $r_{0s}$ of the light reflected from the surface of the Si substrate 201.

$$R_p=(r_{0p}+r_{1p}\exp(-2i\delta))/(1+r_{0p}\cdot r_{1p}\exp(-2i\delta))$$

$$R_s=(r_{0s}+r_{1s}\exp(-2i\delta))/(1+r_{0s}\cdot r_{1s}\exp(-2i\delta)),$$

wherein $\delta=2\pi n_1 t \cos\theta_1/\lambda$.

Consequently, $$R_p/R_s=\tan(\psi)\cdot\exp(-i\Delta)$$

which is used to calculate $\cos\Delta$ and $\tan\psi$ for each wavelength, thereby obtaining a wavelength dependent spectrum. Thereafter, by using a film thickness value t of the oxide film 201 as a parameter, the measured spectrum and the theoretical spectrum are compared to thereby calculate the film thickness value t.

Additionally, when the oxide film 201 formed on the Si substrate 202 has a grating structure as shown in FIG. 4, a cross sectional shape of the grating structure can be also measured by using the ellipsometer and, further, as shown in FIG. 5, there is a method for finding out the shape by dividing a pattern portion into L equal parts and regarding the grating portion as L layer laminated films. In such method, the cross sectional shape is obtained by a model, wherein there is a mixed layer of dielectric constants of air and the grating structure and nth-order diffracted light is generated at each interface. In this case, as shown in FIG. 5, there is a region where the grating pattern is assumed to repeat itself infinitely. Dividing the grating structure into L layers, the dielectric constant is calculated based on a volumetric ratio of air to the grating portion in each layer. By making a model, wherein when light is projected onto the L layer laminated structure at a predetermined angle, respective nth order diffracted lights of reflection and transmission are generated from each interfacing surface of layers, each amplitude reflectivity of s-polarization component and p-polarization component is calculated. Finally, the cross sectional shape can be obtained from wavelength dependency of $\cos\psi$ and $\tan\psi$.

Both of the aforesaid film thickness measuring method and cross sectional shape measuring method are applicable to a case where a substrate surface (a reflective surface of a lower layer) is formed of material having a large absorption coefficient k for light (less light-transmissive material) such as Si, Al and Cu and a film is thick, even and non-transmissive.

However, in the aforementioned film thickness measuring method and cross sectional shape measuring method, there is a drawback that a film thickness and a cross sectional shape cannot be measured in case of a sample having a multilayer interconnection structure in a lower layer of an oxide film as a measurement target.

That is, for example, a sample shown in FIGS. 6A to 6C includes a layer formed of an oxide film 301 as a target of film thickness measurement; b layer formed of metal interconnection 302 and an interlayer insulating film 303 therebelow; and c layer formed of metal interconnection 304 and an interlayer insulating film 305 therebelow, as illustrated in FIG. 6A, and has a multilayer interconnection structure with the metal interconnection 302 of the b layer formed to be orthogonal to the metal interconnection 304 of the c layer. In such multilayer interconnection structure, the oxide film 301 and the interlayer insulating films 303 and 305 are formed of highly light-transmissive material such as silicon dioxide and the metal interconnections 302 and 304 are formed of less light-transmissive material such as Cu, Al and W.

Further, reference numerals 306 and 307 of FIG. 6A are stopper layers formed of a SiN film or a SiC film and used in a CMP(Chemical Mechanical Polishing) process.

In addition, in case of a sample shown in FIG. 7 the oxide film 301 has a grating structure.

In the sample having the aforementioned multilayer interconnection structure, although a theoretical spectrum is calculated by assuming that light is reflected from the surface of the a layer and the interface between the a layer and the b layer or that light is reflected from the surface of the a layer and the interface between the b layer and the c layer, the film thickness and the cross sectional shape cannot be measured due to a complicated structure of the reflective surface of the lower layer.

Accordingly, conventionally, when measuring a thickness of a film formed on a multilayer interconnection structure, after a test piece wafer is loaded during a manufacturing process in addition to a product wafer and a film as a measurement target is formed on the test piece wafer (bear Si), a film thickness is measured by an optical method.

In the same manner, in measuring an etching shape, after loading the test piece wafer and performing a process such as film forming, resist coating, exposure and etching, a cross section is observed by SEM, thereby controlling a shape thereof.

For this reason, in any case, there is a drawback that the manufacturing cost becomes increased, as the number of test piece wafers is increased.

Furthermore, after forming a monitoring pattern for measuring the film thickness or the etching shape in a chip, the position thereof can be measured by using a conventional method. However, in the trend of high integration of IC, it is difficult to provide a monitoring pattern of a predetermined size in the chip. Moreover, granted that it is provided, there is a drawback that dishing, which means that the surface of the metal interconnection 302 is abraded into a bowl shape, occurs in a CMP process due to a large size of the pattern, as shown in FIG. 8, and measurement accuracy becomes deteriorated in case of measuring the film thickness and the like by having an interface with the metal interconnection 302 as a reflective surface.

Therefore, in order to measure and control the thickness and the cross sectional shape of the film formed on the multilayer interconnection, it is required to develop a method for nondestructively measuring any position of a product wafer with high throughput.

SUMMARY OF THE INVENTION

It is, therefore, an object of the present invention to provide a polarization analyzing method for measuring a film thickness or a cross sectional shape of a film formed on multilayer interconnection nondestructively with high throughput.

In accordance with the present invention, there is provided a polarization analyzing method, including the steps of: obtaining reference data by theoretical calculation of values based on a phase difference $\Delta$ and an amplitude ratio $\psi$ of a p-polarization component to an s-polarization component of a light reflected from an object to be measured when illuminating an elliptically polarized incident light of a predetermined wavelength on the object to be measured having a film as a measurement target on a surface thereof at a specified incident angle; and measuring values based on a phase difference $\Delta$ and an amplitude ratio $\psi$ of a p-polarization component to an s-polarization component of a light reflected when actually illuminating the incident light on the object to be measured and comparing the measured values with the reference data to analyze the film, wherein in obtaining the reference data the theoretical calculation is carried out by using a reflective surface of the p-polarization component and a reflective surface of the s-polarization component differing from each other.

Further, the comparing may be performed based on at least two wavelengths.

Still further, the comparing may be performed based on at least two incident angles.

Still further, the values based on the phase difference $\Delta$ and the amplitude ratio $\psi$ may be cos $\Delta$ and tan $\psi$, respectively.

Still further, the object to be measured may contain: an uppermost first layer formed of a highly light-transmissive material; a second layer provided under the first layer and formed of a highly light-transmissive material and a less light-transmissive material; a third layer provided under the second layer and formed of a highly light-transmissive material; and a substrate provided under the third layer and formed of a less light-transmissive material.

Still further, the second layer may have a linear interconnection structure in which the highly light-transmissive material and the less light-transmissive material are disposed alternately in a layer plane direction, and a polarization plane of the p-polarization component is parallel to the linear interconnection.

Still further, a fourth layer may be provided between the substrate and the third layer and have at least on a surface thereof a linear interconnection structure in which a highly light-transmissive material and a less light-transmissive material are disposed alternately in a layer plane direction, and a linear interconnection direction of the fourth layer may be normal to a linear interconnection direction of the second layer.

Still further, the s-polarization component may be reflected from the second layer, and the p-polarization component may be transmitted through the second layer and reflected from the fourth layer.

Still further, the second layer in the theoretical calculation may have respective refractive indexes for the s-polarization component and the p-polarization component different from each other.

Still further, the highly light-transmissive material may be a metal interconnection material and the less light-transmissive material may be an insulating material.

Still further, at least one of a film thickness, a refractive index and a cross sectional shape of the film as the measurement target may be measured.

BRIEF DESCRIPTION OF THE DRAWINGS

The above and other objects and features of the present invention will become apparent from the following description of preferred embodiments, given in conjunction with the accompanying drawings, in which.

DETAILED DESCRIPTION OF THE PREFERRED EMBODIMENTS

Hereinafter, a preferred embodiment of the present invention will be described in detail with reference to accompanying drawings.

Figure 1A:
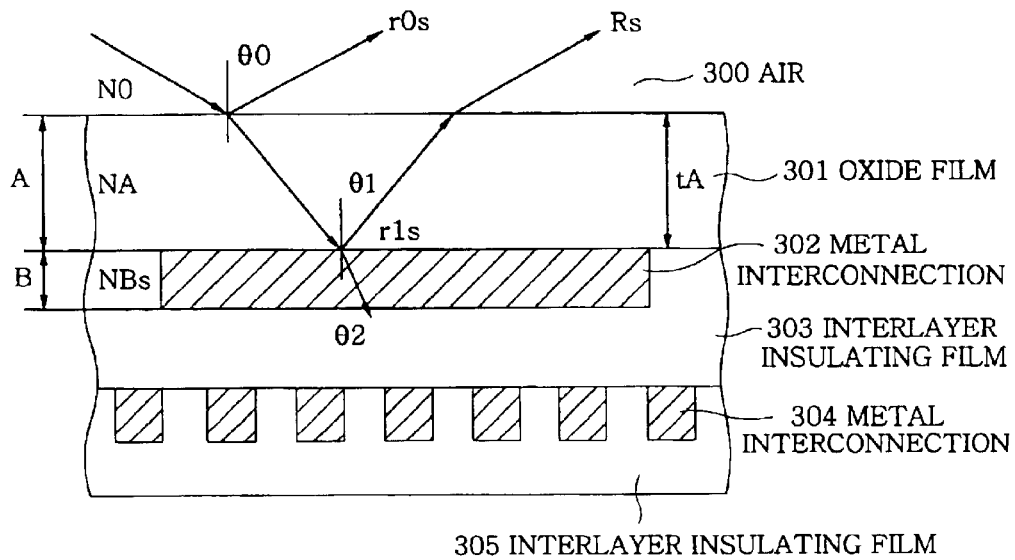
FIGS. 1A and 1B show diagrams for explaining a preferred embodiment of a measuring method of the present invention.
Figure 1B:
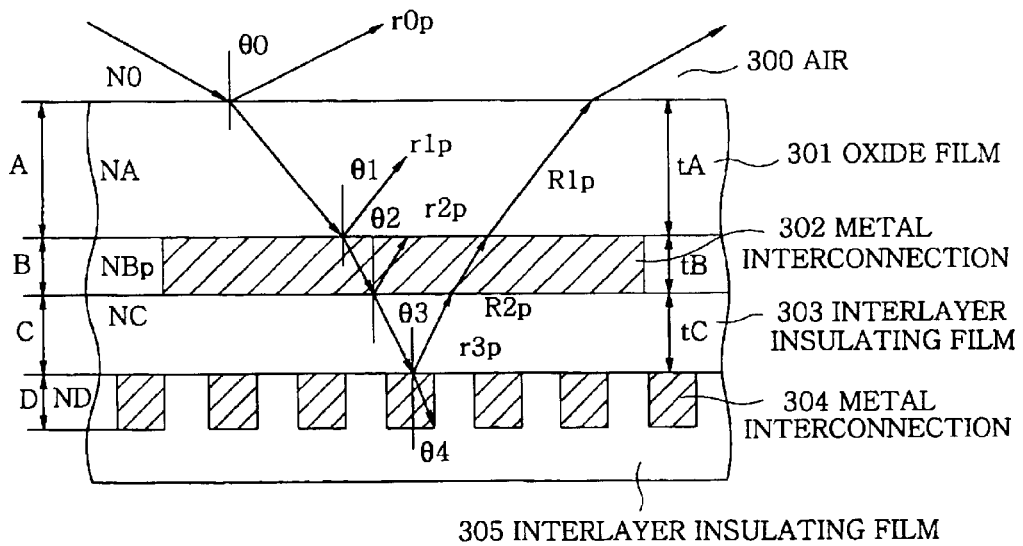
Figure 2:
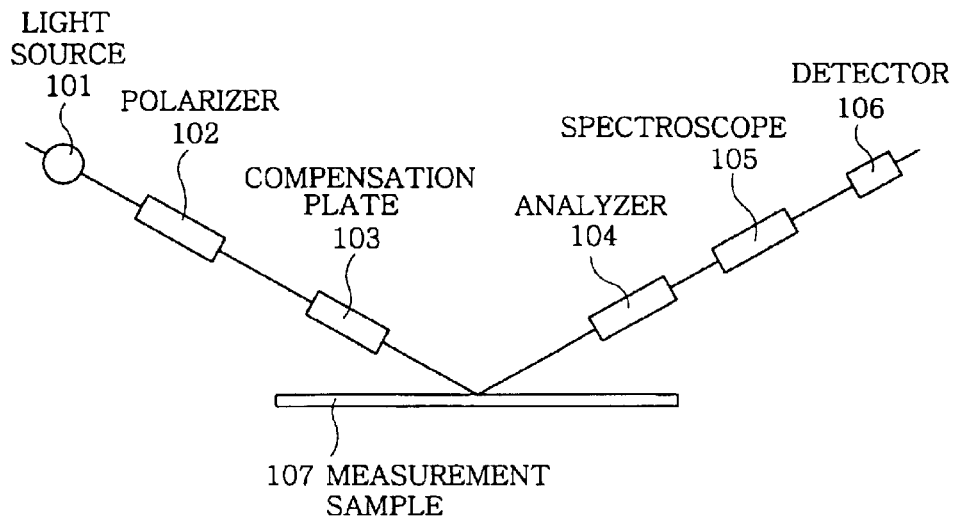
FIG. 2 illustrates a schematic configuration of an ellipsometer used in the method of the present invention.
Figure 3:
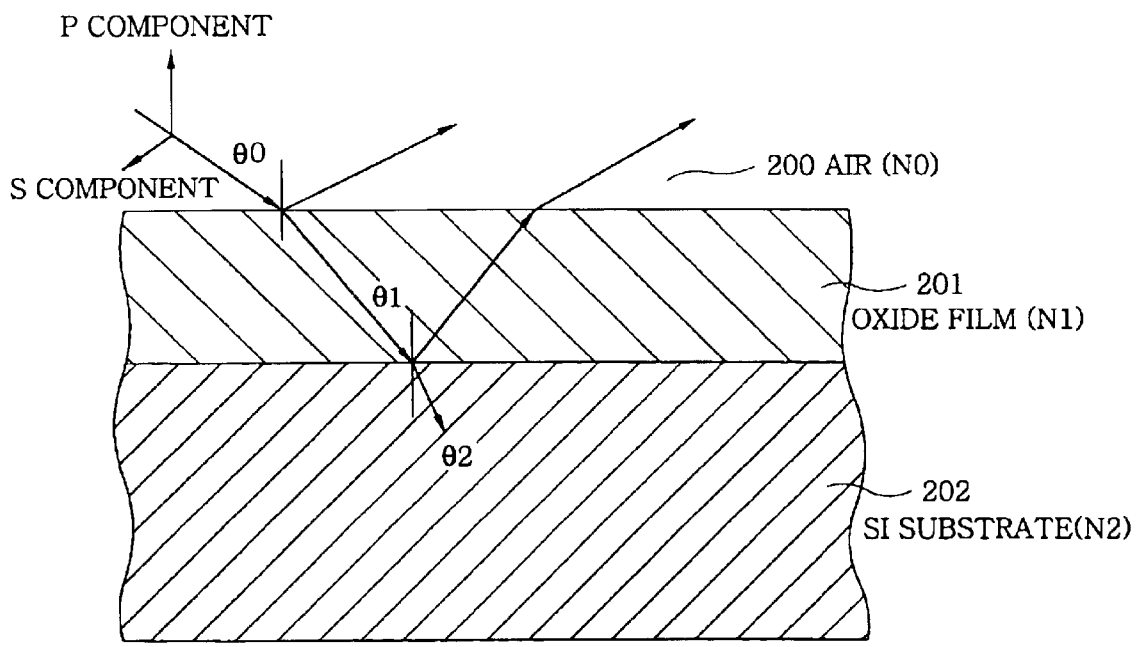
FIG. 3 describes a schematic cross sectional view of a substrate for explaining a conventional method for measuring a film thickness.
Figure 4:
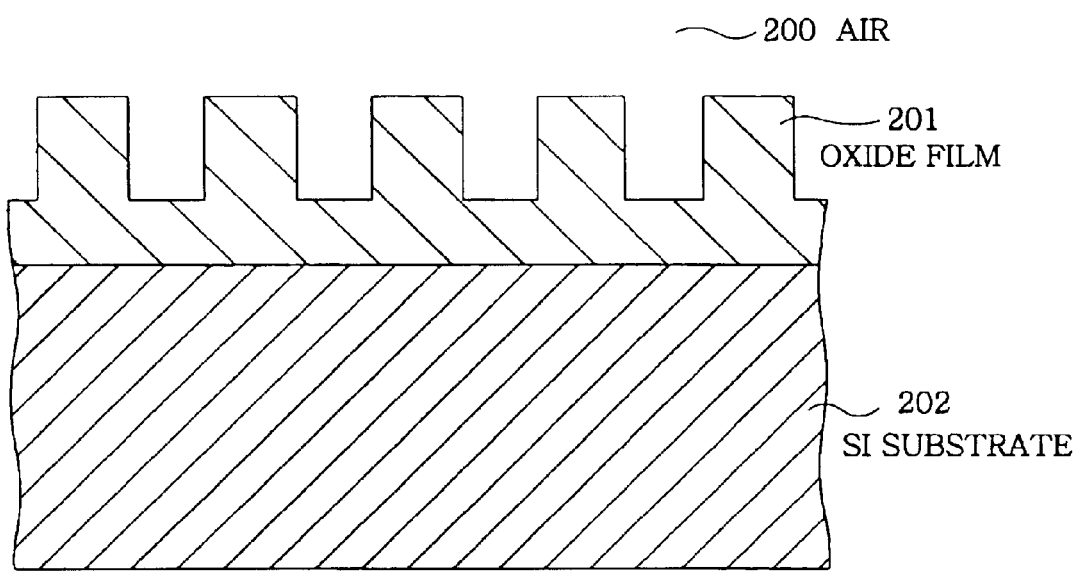
FIG. 4 offers a schematic cross sectional view of a substrate for explaining a conventional method for measuring a cross sectional shape.
Figure 6A:
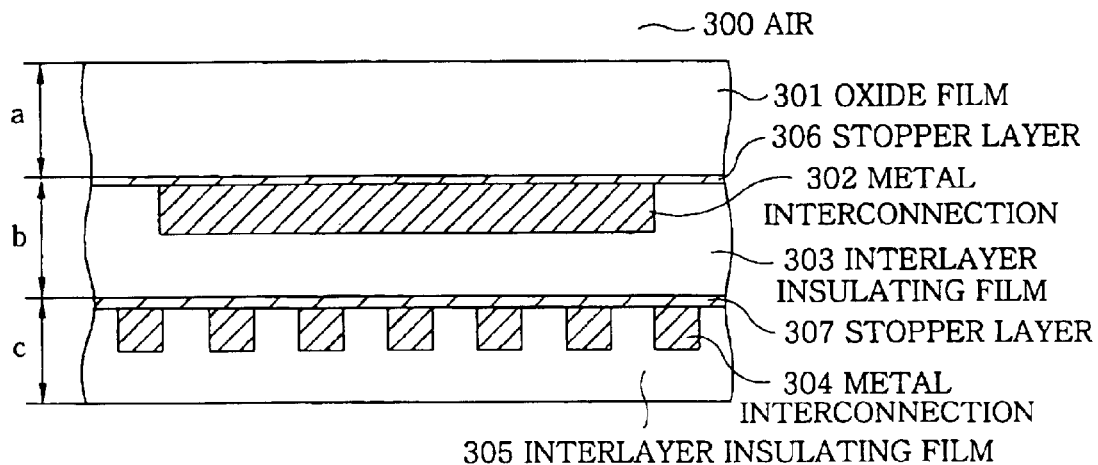
FIGS. 6A to 6C present schematic cross sectional views of a substrate for explaining drawbacks of prior art.
Figure 6B:
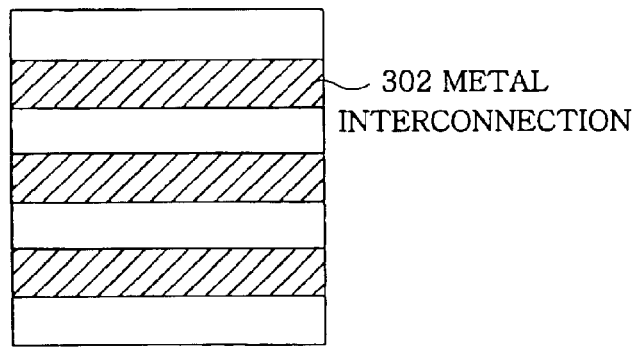
Figure 6C:
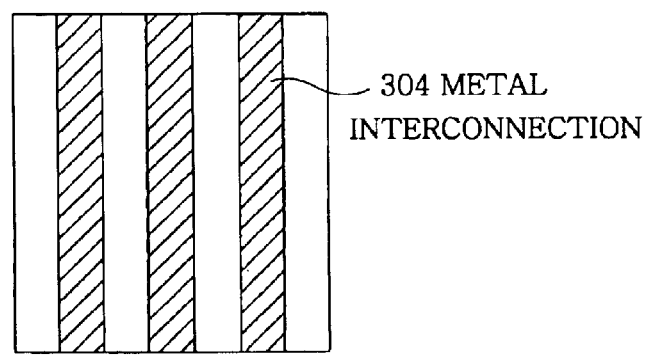

FIGS. 1A and 1B illustrate an explanatory measurement of a film thickness tA of the oxide film 301 of a sample having a multilayer interconnection structure shown in FIG. 6A, and stopper layers shown in FIG. 6A are omitted therein to simplify the description. Further, FIGS. 1A and 1B show movements of an s-polarization component and a p-polarization component of illuminated light, respectively. Furthermore, an ellipsometer used in the measurement includes, as shown in FIG. 2, a light source 101, a polarizer 102, a compensation plate 103, an analyzer 104, a spectroscope 105, and a detector 106.

As shown in FIG. 1A, incident light is illuminated on A layer formed of an oxide film 301 of a refractive index NA from air 300 of a refractive index N0. Further, a part of s-polarization component thereof is reflected from a surface of the A layer at a reflection angle θ0 (r0s) and the remainder thereof is transmitted into the A layer.

Then, the s-polarization component transmitted into the A layer passes through the A layer and reaches an interface with B layer formed of metal interconnection 302 and an interlayer insulating film 303. However, since the s-polarization component oscillates in a direction perpendicular to an interconnection direction (a length direction of the interconnection) of the metal interconnection 302, the s-polarization component cannot pass through a region including the interlayer insulating film 303 formed between the metal lines of interconnection 302 of the B layer and is reflected from the interface with the B layer at a reflection angle θ1. An amplitude reflectivity r1s of the reflected light is:

$$r1s = (NA \cos \theta1 - NBs \cos \theta2)/(NA \cos \theta1 + NBs \cos \theta2),$$

wherein NBs is a refractive index of the B layer for the s-polarization component.

The reflected light r1s passes through the A layer and interferes with the reflected light r0s from the surface of the A layer. An amplitude reflectivity Rs of the interfered light is:

$$Rs = (r0s + r1s \exp(-2i\delta))/(1 + r0s \cdot r1s \exp(-2i\delta)),$$

wherein $\delta = 2\pi$ NA tA cos θ1/λ

$$r0s = (N0 \cos \theta0 - NA \cos \theta1)/(N0 \cos \theta0 + NA \cos \theta1).$$

On the other hand, FIG. 1B shows a movement of the p-polarization component of the illuminated light. A part of the p-polarization component of the incident light, which is illuminated on the A layer formed of the oxide film 301 of the refractive index NA from the air 300 of the refractive index N0, is reflected from the surface of the A layer at the reflection angle θ0 (r0s) and the remainder thereof is transmitted into the A layer.

Thereafter, the p-polarization component transmitted into the A layer passes through the A layer and reaches the interface with the B layer formed of the metal interconnection 302 and the interlayer insulating film 303. Since the p-polarization component oscillates in a direction parallel to an interconnection direction (a length direction of the interconnection) of the metal interconnection 302, the p-polarization component can pass through the region including the interlayer insulating film 303 formed between the metal lines of interconnection 302 of the B layer. Further, the transmitted p-polarization component passes through C layer formed of only the interlayer insulating film 303 and reaches the interface with D layer formed of metal interconnection 304 and an interlayer insulating film 305. Furthermore, as shown in FIG. 1B, a part of the p-polarization component is reflected from the interface with the B layer and another part from the interface with the C layer at reflection angles θ1 and θ2, respectively.

Since the metal interconnection 304 of the D layer are perpendicular to an oscillating direction of the p-polarization component, the p-polarization component cannot pass through a region including the interlayer insulating film 305 formed between the metal lines of interconnection 304 of the D layer and the p-polarization component which reaches the interface with the D layer is reflected therefrom at a reflection angle θ3. An amplitude reflectivity r3p of the reflected light is:

$$r3p = (ND \cos \theta3 - NC \cos \theta4)/(ND \cos \theta3 + NC \cos \theta4)$$

Since the B layer for the s-polarization component and the D layer for the p-polarization component substantially serve as a substrate surface (a non-transmissive surface), it is concluded that NBs, a refractive index of the B layer for the s-polarization component is equal to ND, a refractive index of the D layer for the p-polarization component (ND=NBs) when the metal interconnections of the B layer and the D layer are of the same width and spacing.

The reflected light r3p from the interface with the D layer passes through the C layer and interferes with the reflected light r2p from the interface with the C layer. An amplitude reflectivity R2p of the interfered light is:

$$R2p = (r2p + r3p \exp(-2i\delta))/(1 + r2p \cdot r3p \exp(-2i\delta)),$$

wherein $\delta = 2\pi$ NC tC cos θ3/λ

$$r2p = (NC \cos \theta2 - NBp \cos \theta3)/(NC \cos \theta2 + NBp \cos \theta3).$$

Herein, NBs has been defined as the refractive index of the B layer before when calculating the s-polarization component, but the B layer includes metal such as Cu, W and Al whose refractive index varies depending on a film thickness. Such layer will have a different refractive index when serving as a substrate surface (a non-transmissive surface) for the s-polarization component from a refractive index when serving as a transmissive film for the p-polarization component (NBs□NBp).

In the same way, when the above-mentioned interfered light R2p passes through the B layer, an amplitude reflectivity R1p in the B layer is:

$$R1p = (r1p + R2p \exp(-2i\delta))/(1 + r1p \cdot R2p \exp(-2i\delta)),$$

wherein $\delta = 2\pi$ NBp tB cos θ2/λ

$$r1p = (NBp \cos \theta1 - NA \cos \theta2)/(NBp \cos \theta1 + NA \cos \theta2).$$

Finally, an amplitude reflectivity Rp in the surface of the A layer is:

$Rp=(r0p+R1p \exp(-2i\delta))/(1+r0p \cdot R1p \exp(-2i\delta))$, wherein $\delta=2\pi$ NA tA cos $\theta 1/\lambda$ $r0p=(NA \cos \theta 0-N0 \cos \theta 1)/(NA \cos \theta 0+N0 \cos \theta 1)$.

By doing this, from each amplitude reflectivity of Rs and Rp which are respectively calculated for the s-polarization component and the p-polarization component in the reflective surface serving as the substrate surface (the non-transmissive surface), functions of amplitude ratio $\psi$ of the p-polarization component to the s-polarization component and phase difference $\Delta$ between the s-polarization component and the p-polarization component, i.e., $\tan\psi$ and $\cos\Delta$ can be calculated from the following equation.

$Rp/Rs=\tan\psi \cdot \exp(-i\Delta)$

The above description is for an arbitrary wavelength $\lambda$, and $\tan\psi$ and $\cos\Delta$ are calculated for a plurality of continuous wavelengths, whereby spectrum data of $\lambda$-$\tan\psi$ and $\lambda$-$\cos\Delta$ serving as reference data can be obtained.

Thereafter, with regard to a film thickness tA of a different A layer, the spectrum data of the reference data as obtained above is compared with spectrum data obtained by actual measurement by assigning parameters for film thickness and film quality and a film thickness that minimizes or maximizes a statistical error function thereof is outputted as a measured film thickness of the oxide film 301 (A layer) formed on the multilayer interconnection.

Further, the sample may be rotated 90 degrees and, that is, a pattern wherein the respective roles of the s-polarization component and the p-polarization component on reflection and transmission are reversed is possible.

Figure 5:
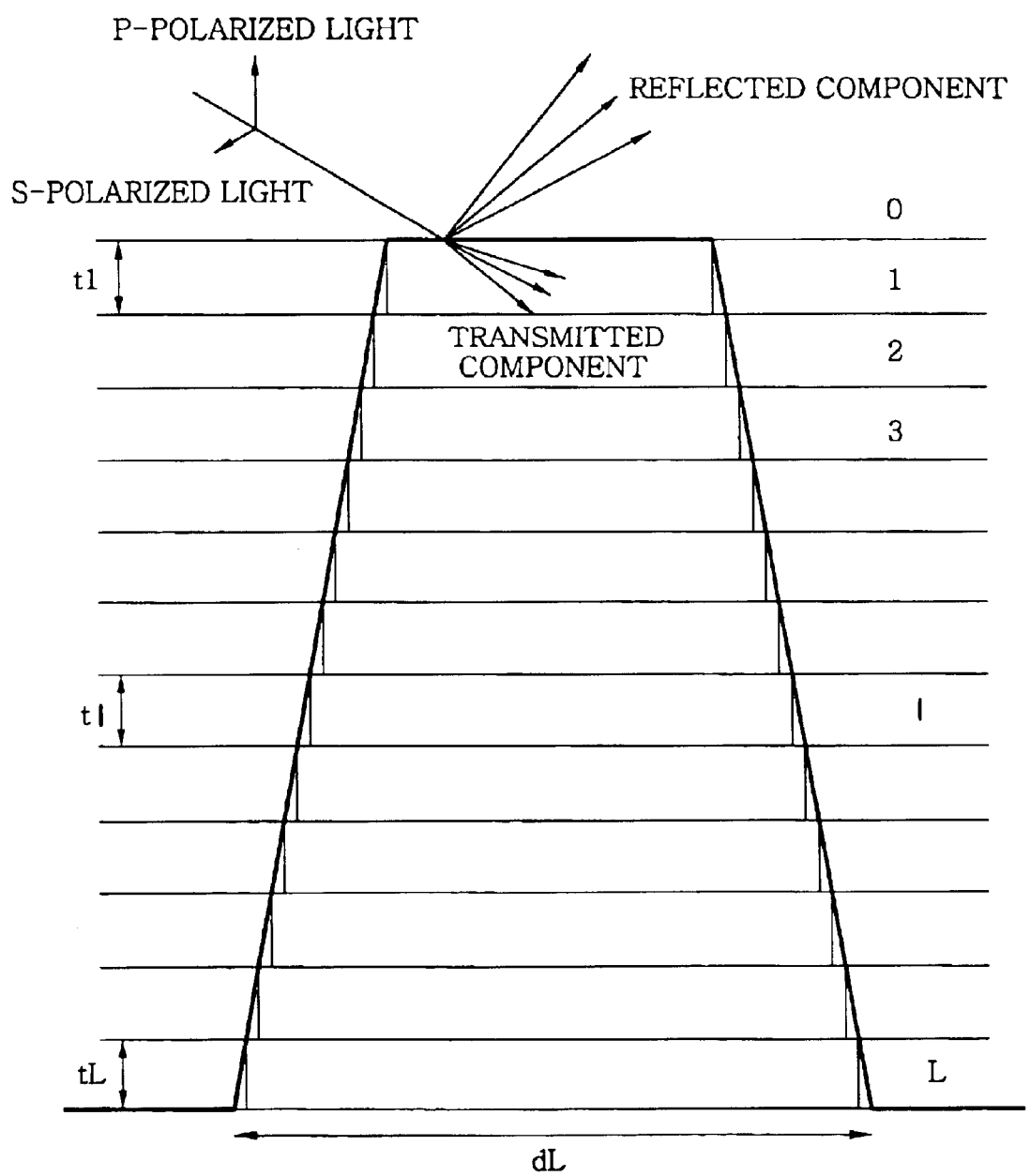
FIG. 5 provides a schematic cross sectional view of a substrate for explaining a conventional method for measuring a cross sectional shape.
Figure 7:
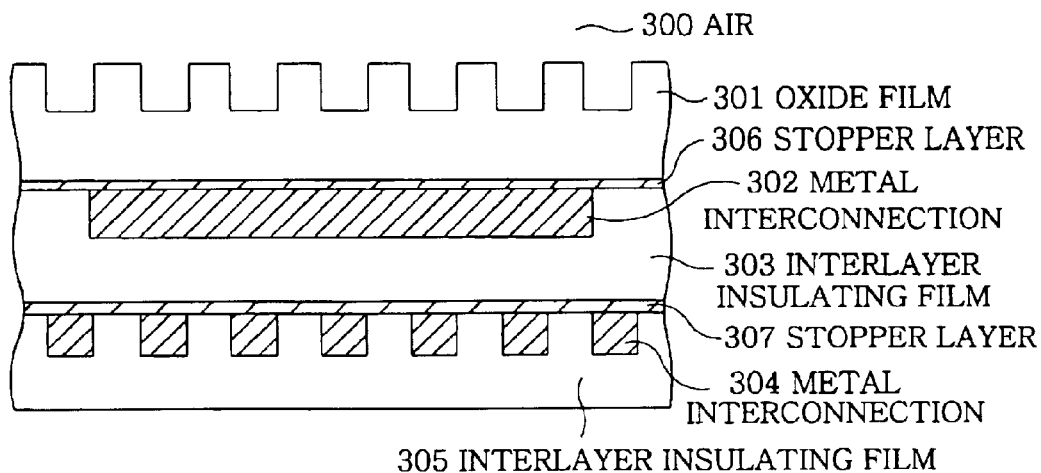
FIG. 7 depicts a schematic cross sectional view of a substrate for explaining drawbacks of prior art.
Figure 8:
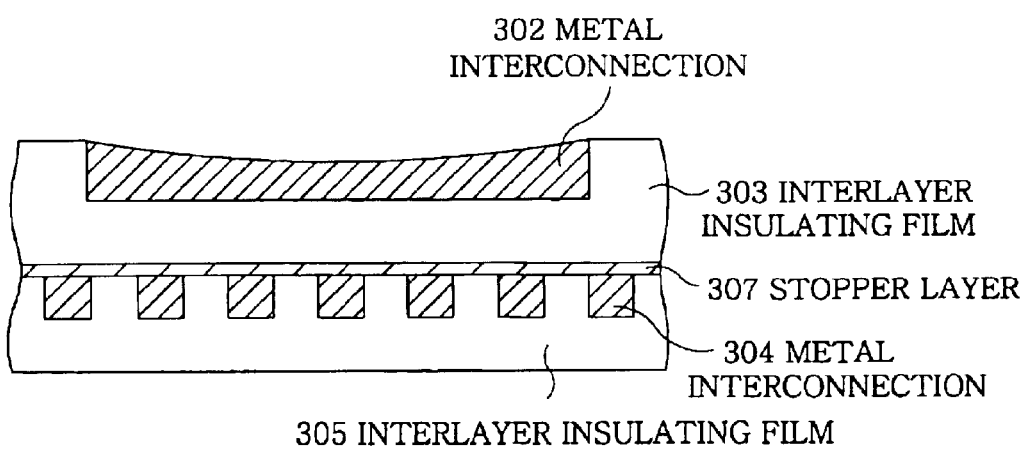
FIG. 8 represents a schematic cross sectional view of a substrate for explaining drawbacks of prior art.

Furthermore, as described above, the method of calculating wavelength dependency of $\tan \psi$ and $\cos \Delta$ by assuming that the s-polarization component and the p-polarization component are respectively reflected from different surfaces and comparing spectrum data obtained by actual measurement therewith is applicable to cross sectional shape measurement such as etching shape measurement in the grating structure as shown in FIG. 7. With regard to obtaining a cross sectional shape of a top layer, there is employed a method for obtaining the shape by dividing a pattern portion into n equal parts and regarding the grating portion as n layer laminated films as shown in FIG. 5.

Still further, in the above embodiment, the metal interconnection 302 and the metal interconnection 304 which are orthogonal to each other are formed in the B layer and the D layer, respectively, but the present invention is also applicable to a structure including D layer as a lower layer formed of a non-transmissive surface such as a substrate surface in place of the metal interconnection 304.

Moreover, by varying an incident angle in lieu of a wavelength, the same effect can be obtained. For example, by making measurement while varying the incident angle $\theta 0$ in FIG. 1, respective dependencies of $\tan\psi$ and $\cos\Delta$ on incident angle can be obtained. Then, by calculating for a multiplicity of incident angles based on the above equations, reference data for $\theta$–$\cos \Delta$ and $\theta$–$\tan \psi$ can be obtained. By comparing the reference data and the spectrum data from actual measurement, it is possible to obtain physical quantities for desired film thickness and cross sectional shape.

As describe above, in accordance with the present invention, a thickness and a cross sectional shape of a film formed on multilayer interconnection can be nondestructively measured with high throughput.

While the invention has been shown and described with respect to the preferred embodiments, it will be understood by those skilled in the art that various changes and modifications may be made without departing from the spirit and scope of the invention as defined in the following claims.

Industrial Applicability

The polarization analyzing method in accordance with the present invention can be employed in the semiconductor manufacturing industry for manufacturing semiconductor devices. Thus, it has an industrial applicability.

What is claimed is:

1. A polarization analyzing method, comprising the steps of:

obtaining reference data from theoretical calculation of values based on a phase difference $\Delta$ between a p-polarization component and an s-polarization component and an amplitude ratio $\psi$ of a p-polarization component to an s-polarization component of a light reflected from an object to be measured when illuminating an elliptically polarized incident light of a predetermined wavelength on the object to be measured having a film as a measurement target on a surface thereof at a specified incident angle; and measuring values based on a phase difference $\Delta$ between a p-polarization component and an s-polarization component and an amplitude ratio $\psi$ of a p-polarization component to an s-polarization component of a light reflected when actually illuminating the incident light on the object to be measured and comparing the measured values with the reference data to analyze the film, wherein in obtaining the reference data the theoretical calculation is carried out by using a reflective surface of the p-polarization component and a reflective surface of the s-polarization component differing from each other.

2. The method of claim 1, wherein said comparing is performed based on at least two wavelengths.

3. The method of claim 1, wherein said comparing is performed based on at least two incident angles.

4. The method of claim 1, wherein the values based on the phase difference $\Delta$ and the amplitude ratio $\psi$ are $\cos \Delta$ and $\tan\psi$, respectively.

5. The method of claim 1, wherein the object to be measured includes:

an uppermost first layer formed of a highly light-transmissive material;

a second layer provided under the first layer and formed of a highly light-transmissive material and a less light-transmissive material;

a third layer provided under the second layer and formed of a highly light-transmissive material; and a substrate provided under the third layer and formed of a less light-transmissive material.

6. The method of claim 5, wherein the second layer has a linear interconnection structure in which the highly light-transmissive material and the less light-transmissive material are disposed alternately in a layer plane direction, and a polarization plane of the p-polarization component is parallel to the linear interconnection.

7. The method of claim 6, wherein a fourth layer is provided between the substrate and the third layer and has at least on a surface thereof a linear interconnection structure in which a highly light-transmissive material and a less light-transmissive material are disposed alternately in a layer plane direction, and a linear interconnection direction of the fourth layer is normal to a linear interconnection direction of the second layer.

8. The method of claim 7, wherein the s-polarization component is reflected from the second layer, and the p-polarization component is transmitted through the second layer and reflected from the fourth layer.

9. The method of claim 5, wherein the second layer in the theoretical calculation has different refractive indexes for the s-polarization component and the p-polarization component, respectively.

10. The method of claim 5, wherein the highly light-transmissive material is an insulating material and the less light-transmissive material is a metal interconnection material.

11. The method of claim 1, wherein at least one of a film thickness, a refractive index and a cross sectional shape of the film as the measurement target is measured.

* * * * *